United States Patent [19]

Rowland

[11] Patent Number: 4,516,424
[45] Date of Patent: May 14, 1985

[54] OXYGEN CONCENTRATOR MONITOR AND REGULATION ASSEMBLY

[75] Inventor: Robert O. Rowland, Hemet, Calif.

[73] Assignee: Hudson Oxygen Therapy Sales Company, Temecula, Calif.

[21] Appl. No.: 396,705

[22] Filed: Jul. 9, 1982

[51] Int. Cl.³ ............................................. G01N 31/06
[52] U.S. Cl. ........................................ 73/23; 73/1 G; 55/21
[58] Field of Search ................ 73/23, 1 G; 55/58, 21, 55/25, 26; 128/205.12, 202.26; 340/632

[56] References Cited

U.S. PATENT DOCUMENTS

| | | | |
|---|---|---|---|
| 2,944,627 | 7/1960 | Skarstrom | 55/33 |
| 3,070,988 | 1/1963 | Kapff et al. | 73/1 G |
| 3,142,547 | 7/1964 | Marsh et al. | 55/58 |
| 3,280,536 | 10/1966 | Berlin | 55/58 |
| 3,898,047 | 8/1975 | Cramer | 128/202.26 |
| 3,922,149 | 11/1975 | Ruder et al. | 55/21 |
| 4,065,272 | 12/1977 | Armond | 55/58 |
| 4,150,670 | 4/1979 | Jewett et al. | 73/23 |
| 4,197,095 | 4/1980 | White, Jr. et al. | 55/21 |
| 4,247,311 | 1/1981 | Seibert et al. | 55/163 |
| 4,376,640 | 3/1983 | Vo | 55/58 |
| 4,384,925 | 5/1983 | Stetter et al. | 73/1 G |
| 4,404,005 | 9/1983 | Hamlin et al. | 55/163 |
| 4,428,372 | 1/1984 | Beysel et al. | 55/21 |
| 4,449,990 | 5/1984 | Tedford, Jr. | 55/26 |

FOREIGN PATENT DOCUMENTS 2029257 3/1980 United Kingdom .

Primary Examiner—Stephen A. Kreitman
Attorney, Agent, or Firm—Seiler, Quirk & Tratos

[57] ABSTRACT

An improved oxygen concentrator includes an oxygen sensor, valve and timer for periodically directing a breathable gaseous mixture having increased oxygen concentration to the sensor. A preferred assembly includes an alarm and means for increasing oxygen concentration in the breathable gaseous mixture when the concentration falls below a selected concentration.

29 Claims, 1 Drawing Figure

OXYGEN CONCENTRATOR MONITOR AND REGULATION ASSEMBLY

BACKGROUND OF THE INVENTION

Recently oxygen concentrators have become used extensively for home care patients. Oxygen therapy using breathable gaseous mixtures containing relatively high oxygen concentrations of between about 80 and about 95% is highly advantageous in treating chronic respiratory or pulmonary ailments. As an alternative to the use of oxygen cylinders which have to be frequently replaced and refilled, oxygen concentrators are more convenient, simple to operate, and economical.

Oxygen concentrators used today are of the type in which atmospheric air is pumped through a molecular sieve bed from which gas nitrogen is adsorbed resulting in a gaseous mixture having substantially increased oxygen concentration. The gas is then delivered usually through a nasal cannula, a patient often requiring the increased oxygen delivery much of the time, if not exclusively. Because most patients require a reasonably specific selected concentration of oxygen in the breathable gaseous mixture, the ability of the apparatus which supplies the oxygen to maintain continuous delivery of the necessary concentrations is important. Where oxygen concentrations fall below selected or required limits, substantial patient injury may result. With oxygen concentrator devices presently used, the oxygen concentration being delivered by the apparatus is unknown to the patient. Thus, the apparatus may malfunction without the user's knowledge, possibly resulting in substantial injury before the malfunction is even realized. Even when the apparatus is provided with alarms, present methods of sensing oxygen in the device is unsatisfactory because of extremely low sensor life. Moreover, when low concentrations are sensed, the apparatus simply becomes useless since specialized technicians are usually required to repair the malfunction before suitable oxygen concentration deliveries can be resumed. It is to the elimination of the aforesaid problems and disadvantages that the improved apparatus of the present invention is directed.

SUMMARY OF THE INVENTION

The improved oxygen concentrator of the present invention incorporates a three-way valve which is regulated by a timer for periodically directing the gaseous mixture having high oxygen concentration to an oxygen sensor. In the preferred embodiment, the apparatus includes means for changing the time in which atmospheric air is exposed to the molecular sieve bed whereby selected oxygen concentrations can be maintained automatically by the apparatus. These as well as other advantages will be evident from the following detailed description.

DETAILED DESCRIPTION OF THE INVENTION

Figure 1:
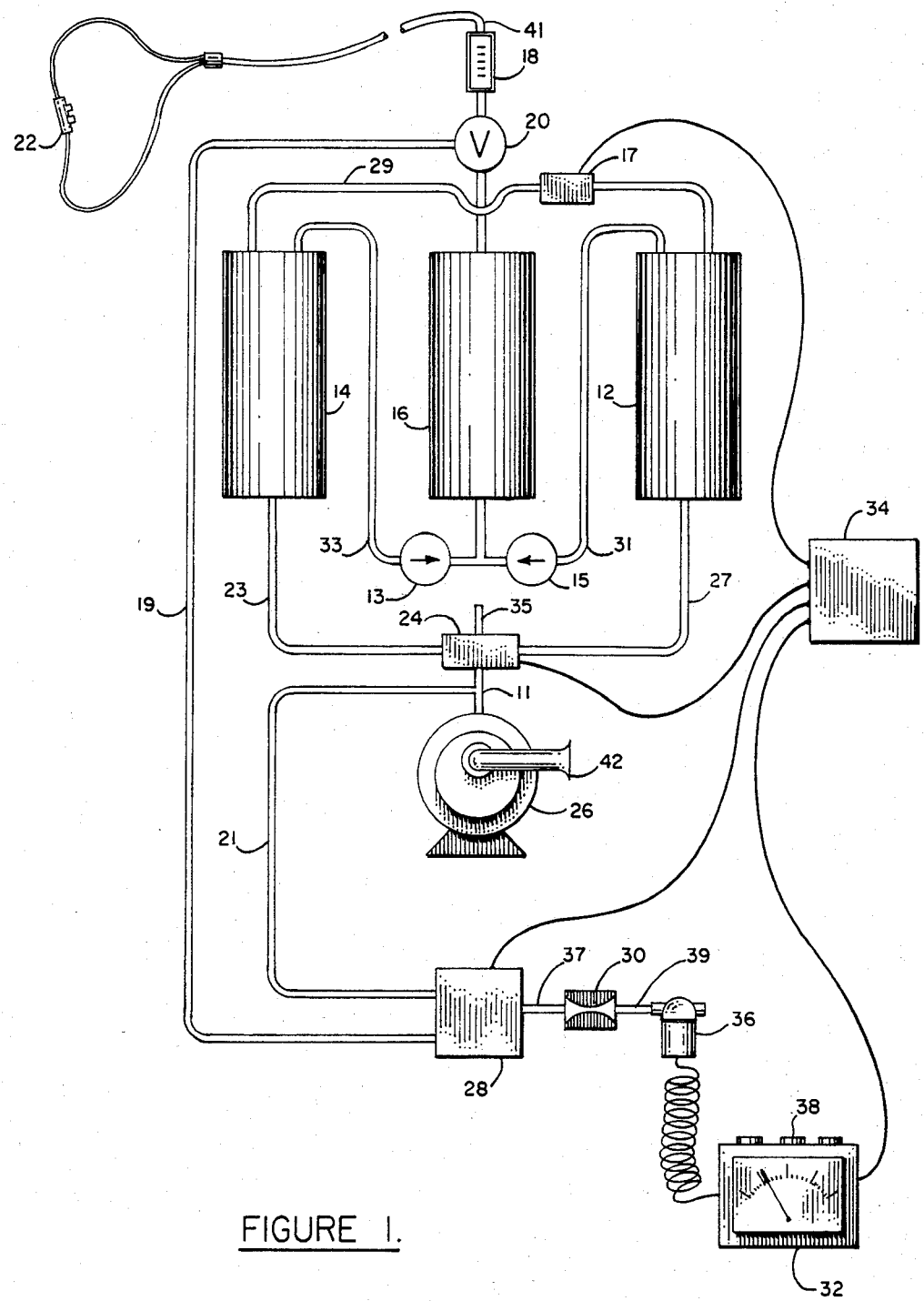
FIG. 1 illustrates schematically the improved oxygen concentrator apparatus of the invention including oxygen concentration sensing components.

In the drawing there is illustrated generally the oxygen concentrator apparatus. The apparatus includes a compressor 26 which forces atmospheric air under pressure alternately into cannisters 12 and 14 in which are provided molecular sieve beds containing suitable adsorbants for nitrogen. Between the molecular sieve bed cannisters is a container 16 acting as a reservoir for holding oxygen enriched gas generated by the two cannisters. Extending between the cannisters and the reservoir are conduits or pipes including valves for directing the gas between the cannisters and to the reservoir.

Generally, in operation, atmospheric air is drawn into compressor 26 via inlet pipe 33 on the suction side of the compressor. From the pressure side of the compressor air is forced via pipe 11 to valve 24 where it is alternately directed to cannisters 12 and 14. Four-way valve 24 alternately directs the gas to the cannisters based on a time cycle regulated by controller 34. The atmospheric air is directed to cannister 12 via conduit 27, and nitrogen is adsorbed from the air as pressure in the vessel increases. The oxygen enriched gas remains in cannister 12 until reduced gas pressure in reservoir 16 is reached, causing the gas to flow into reservoir 16 via conduit 31 through one-way valve 15. Pressure in the reservoir is reduced as oxygen enriched gas is directed therefrom for patient use via valve 20. After a selected time, valve 24 switches the gas flow and directs air to cannister 14 via conduit 23 with the oxygen enriched gas passing into reservoir 16 via pipe 33 and one-way valve 13 as previously described. After a cannister has gone through a pressurized nitrogen adsorbtion cycle pressure is relieved to cause release of the adsorbed nitrogen, which nitrogen enriched gas is then vented to atmosphere by valve 24 via outlet pipe 35. If desired, a vacuum may also be drawn on the cannister to further remove nitrogen. Two-way valve 17 is then opened and the cannister is purged with oxygen enriched gas from the other of the cannisters for a short period of time to remove any residual nitrogen enriched gas. Thus, each cannister alternately adsorbs nitrogen from atmospheric air, the oxygen enriched gas is recovered, and the remaining nitrogen is exhausted so that the cannister is available for another nitrogen adsorbtion cycle. Valve 17 between the cannisters along conduit 29 allows for such purging between the cannisters and is regulated by a second timing function of controller 34. Enriched oxygen containing gas in reservoir 16 is directed via valve 20 to flow meter 18 where it is dispensed to the patient via tube 31 and nasal cannula 22. The general functioning of such oxygen concentrators utilizing the two adsorbtion cannisters containing the molecular sieve beds as well as the nitrogen adsorbtive material itself is disclosed, for example, in U.S. Pat. Nos. 2,944,627, 3,142,547, 3,280,536 and 3,898,047. The specific portions of these patents for further explaining and understanding the operation and components of the oxygen concentrator are incorporated herein by reference.

The improved feature of the invention is in monitoring the oxygen enriched gas directed to a patient from reservoir 16. For this function, three-way valve 28 has a first and second inlet, the first inlet being connected to pipe 19 through which the oxygen enriched gas is directed from valve 20. The second gas inlet is connected to pipe 21 through which atmospheric air is directed from the pressure side of compresser 26. A single gas outlet is connected to pipe 37 which directs gas from the valve to oxygen sensor 36 via flow control orifice 30. Valve 28 preferably includes a solenoid, electrically connected to controller 34, so that the first and second inlets are alternately selectively opened on command from the controller. Thus, one or the other of the inlets will be opened so that gas from either pipe 19 or 21 is always passing through the valve to the outlet and through pipe 37, flow control orifice 30, and analyzed by oxygen sensor 36. Any suitable oxygen sensor may be used such as a fuel cell, or it may be polarographic, or a combination. However, regardless of the type of sensor used, its life is directly proportional to the concentration of oxygen it is monitoring and the length of time which it is actively monitoring. For example, some fuel cells have a life expectancy of approximately 240,000 hours. Since the cell is constantly monitoring oxygen concentration of a gas to which it is exposed, a cell life is substantially increased by limiting the time to which it is exposed to the gaseous mixture containing the high concentration of oxygen. This feature is accomplished by another timer function of controller 34 which regulates the relative times that the first and second gas inlet of valve 28 are opened.

When the first gas inlet is open, the gaseous mixture having the high oxygen concentration from pipe 19 is directed through the valve 28. The first gas inlet may be periodically opened for a relatively short period of time, for example, 30 to 90 seconds every 15 minutes or so. The actual time must be sufficient to purge conduit 37, orifice 30, and sensor 36 of atmospheric air and to adequately sample the oxygen concentration in the oxygen rich mixture. Similarly, when the high oxygen concentration gas has been analyzed, a timer function of controller 34 will cause the solenoid in valve 28 to close the first gas inlet and open the second inlet whereby atmospheric air via pipe 21 will purge the oxygen rich gas from pipe 37, flow control orifice 30, and pipe 39. This atmospheric air will contain substantially less oxygen, approximately 20.9% as opposed to the higher concentrations of say 85 to 96% produced by the oxygen concentrator. During the time atmospheric air is monitored, the sensor will calibrate itself, since the oxygen concentration of air is precisely known. Such a self-calibrating system is an important feature of the apparatus. Moreover, because the sensor is constantly monitoring the oxygen concentration of the gas to which it is exposed, the longer the monitoring of the atmospheric air, or the more the high oxygen concentration gas is sensing is limited, the longer the life of the oxygen sensor.

Another preferred feature of the apparatus is to minimize the amount of gas to be sampled by the sensor to achieve an accurate reading of oxygen concentration. For this purpose a flow control orifice 30, which allows a very low flow of gas therethrough, for example, between about 50 and about 100 cc per minute, and relatively short and/or small diameter pipe 39 between the orifice and sensor 36 is used. Any similar means for minimizing the volume of gas to be accurately sampled may be used.

The oxygen monitor 32 may include a digital readout, scale with pointer or indicator, or the like, or simply a light may be used. Such a monitor preferably includes an alarm circuit in which a visual alarm 38 and/or audible alarm may be incorporated for signaling when oxygen concentration of the high oxygen concentration gas mixture is below a preselected concentration. This alarm will be energized or enabled only when the oxygen sensor is receiving the high oxygen concentration gas through valve 28. Normally such an alarm circuit will be energized after a time delay from the opening of first gas inlet in valve 28, and this function may be regulated by a timer circuit in controller 34, or an independent timer.

Although monitoring of the oxygen enriched gas produced by the apparatus, as previously described, is quite important, means associated with the apparatus for maintaining selected concentration output in response to the monitored concentration, has not been practiced heretofore. Such a system is of substantial benefit and improvement since variation in the oxygen concentration produced by such apparatus often changes over long and continuous periods of use. For example, the ability of the molecular sieve material to adsorb nitrogen begins to deteriorate as soon as its use is initiated. The nitrogen adsorbing efficiency also varies with changes in humidity. Differences in sieve packing density between the cannisters may also cause variation in flow rates between different units. Accordingly, different units, although seemingly substantially identical, may require somewhat different time sequencing between the two and four-way valves in order to maximize performance.

Thus, in another preferred embodiment, the apparatus includes means for changing oxygen concentration by changing the residence or exposure time of atmospheric air in cannisters 12 and 14. To achieve such a function, controller 34 includes means for comparing the oxygen concentration monitored by sensor 36 and/or monitor 32 with a pre-selected reference concentration, and operating valves 24 and 17 in response to changes in the monitored concentration. In this embodiment, controller 34 is operatively connected to sensor 36 or monitor 32 (the latter being shown) and to the two valves, to change the residence or exposure time of air in the respective cannisters. When oxygen concentration being produced falls below the selected concentration for a specified delivery rate, the controller will change the time and period of opening and closing the valves to increase adsorption times as required. Most suitable for such a conroller is a logic circuit or microprocessor cooperating with a memory device, or a microcomputer, and means connected to the controller for operating the valves in response to microprocessor signals, for example, an interface device and drivers such as transistors or solid state relays. Such a controller may be programmed to change the oxygen monitoring times when a sufficient change in concentration in a sample or series of samples, is detected, to achieve accelerated concentration changes. The controller may be connected to monitor 32 and function to operate the valves in response to an alarm signal from the monitor indicating low oxygen concentration, or it may be connected to the monitor or sensor 36 so that the concentration value itself is fed to the controller where it is compared with desired concentration requirements. The controller itself may have an alarm function or be connected to an external alarm, for example, an optional feature of monitor 32, whereby the alarm is set off only after low concentration has been determined from 2 or more successive samplings. Such a controller program will avoid a premature alarm which could otherwise result from a single low sample reading. Thus, by incorporating a controller having such functions, it will be evident that efficiency of the apparatus will be continually monitored and automatically adjusted to maintain production and delivery of suitable oxygen concentrations.

I claim:

1. In an apparatus for increasing the oxygen concentration of a breathable gaseous mixture to be delivered to a patient, the improvement comprising an oxygen sensing assembly for sensing the concentration of oxygen in said breathable gaseous mixture comprising:
   a three-way valve having a first and a second gas inlet and a gas outlet, and means for selectively opening said first and second gas inlets,
   a first conduit connected to said first gas inlet for directing said breathable gaseous mixture having increased oxygen concentration thereto,
   a second conduit connected to said second gas inlet for directing atmospheric air thereto,
   an oxygen sensor,
   a third conduit connected between said gas outlet and said oxygen sensor, and
   a control means electrically connected to said means for alternately opening one of said first and second gas inlets and closing the other, for a selected time, and operating said oxygen sensor.

2. The apparatus of claim 1 including an alarm circuit electrically connected between said control means and said oxygen sensor for signaling when the oxygen concentration falls below a selected value.

3. The apparatus of claim 1 including molecular sieve bed for adsorbing nitrogen from atmospheric air to produce a breathable gaseous mixture having increased oxygen concentration, and wherein said first conduit is connected to a supply of said breathable gaseous mixture.

4. The apparatus of claim 3 including valve means for directing atmospheric air to said molecular sieve bed and operatively connected to said control means whereby said valve means is operated for changing the exposure time of atmospheric air in the molecular sieve bed in response to decrease of oxygen concentration sensed by said oxygen sensor below a selected value.

5. The apparatus of claim 4 wherein said control means comprises a microprocessor device.

6. The apparatus of claim 1 including a gas volume limiting means between said gas outlet and said oxygen sensor.

7. The apparatus of claim 6 wherein said gas volume limiting means include a flow control orifice.

8. The apparatus of claim 1 wherein said oxygen sensor includes calibration means.

9. The apparatus of claim 8 wherein said calibration means calibrates said oxygen sensor with atmospheric air.

10. A method of sensing the concentration of oxygen produced by an oxygen concentrator comprising
   directing separate streams of oxygen produced by said oxygen concentrator and atmospheric air to a valve member,
   alternately directing one of said streams from said valve member to an oxygen sensor, and alternately sensing the amount of oxygen in said stream of oxygen and said atmospheric air, respectively.

11. The method of claim 10 including providing a timing cycle for said valve member whereby each of said streams are alternately directed to said oxygen sensor for a selected time.

12. The method of claim 11 including calibrating said oxygen sensor when atmospheric air is directed thereto.

13. The method of claim 11 including providing a flow restricting means between said valve member and said oxygen sensor for limiting the flow of said streams therebetween.

14. The method of claim 11 including providing alarm means cooperating with said oxygen sensor for indicating a low concentration of oxygen in said stream of oxygen produced by said oxygen concentrator directed to said oxygen sensor.

15. In an oxygen concentrator comprising first and second molecular sieve beds for selectively adsorbing nitrogen from atmospheric air to produce a product gas having a high oxygen concentration, a reservoir for receiving said product gas from said seive beds, a compressor and a valve cooperating therewith for pressurizing said sieve beds with atmospheric air, and means for withdrawing product gas from said reservoir, the improvement comprising:
   an oxygen sensor for sensing the concentration of oxygen of said product gas,
   a control valve having a first and a second gas inlet, a gas outlet, and means for opening and closing said gas inlets,
   means for directing product gas to said first gas inlet and atmospheric air to said second gas inlet, and for directing gas from said gas outlet to said oxygen sensor, and
   control means for selectively opening and closing said first and second gas inlets.

16. The oxygen concentrator of claim 15 wherein said control means include a timer for selectively opening and closing said first and second gas inlets according to a preselected timing cycle.

17. The oxygen concentrator of claim 16 including a gas volume limiting device between said gas outlet and said oxygen sensor.

18. The oxygen concentrator of claim 16 wherein said oxygen sensor includes means for calibration with atmospheric air.

19. The oxygen concentrator of claim 15 including an alarm device electrically connected to said oxygen sensor for signaling when the oxygen concentration of product gas sensed by said oxygen sensor falls below a selected value.

20. In an oxygen concentrator comprising a plurality of molecular sieve beds for alternately receiving atmospheric air and for selectively adsorbing nitrogen therefrom to increase the oxygen concentration of a product gas recovered therefrom, a reservoir for receiving said product gas from said sieve beds, a compressor and a valve cooperating therewith for pressurizing said sieve beds with atmospheric air, valve switching means for alternately charging said sieve beds, and means for withdrawing said product gas from said reservoir, the improvement comprising:
   timing means for switching said valve according to a timing cycle,
   an oxygen sensor for sensing the oxygen concentration of said product gas withdrawn from said reservoir, and control means for selectively directing product gas and atmospheric air to said oxygen sensor, and
   a microprocessor having memory means provided with a selected reference gas product oxygen concentration, means for comparing the product gas oxygen concentration sensed by said oxygen sensor with said selected reference oxygen concentration, and means for adjusting the timing cycle for switching said valve to increase the time for pressurizing said sieve beds to produce a product gas having at least said selected reference oxygen concentration.

21. The oxygen concentrator of claim 20 wherein said control means comprises a control valve electrically connected to said microprocessor.

22. The oxygen concentrator of claim 21 wherein said microprocessor includes timing means for operating said control valve for directing product gas to said oxygen sensor at selected time intervals.

23. An oxygen concentrator for producing a gaseous product having increased oxygen concentration from atmospheric air comprising:

first and second molecular sieve beds for adsorbing nitrogen from said atmospheric air to produce a product gas having a high oxygen concentration, a compressor for charging atmospheric air into said sieve beds, a reservoir for receiving said product gas from said sieve beds, a valve having a first position in which atmospheric air is charged into said first sieve bed from said compressor and simultaneously adsorbed nitrogen is vented from said second sieve bed to substantially remove nitrogen therefrom, and a second position in which atmospheric air is pressurized into said second sieve bed from said compressor and simultaneously adsorbed nitrogen is vented from said first sieve bed to substantially remove nitrogen therefrom, means for withdrawing said product gas from said reservoir, an oxygen sensor for sensing the oxygen concentration of said product gas withdrawn from said reservoir, switching means for switching said valve between said first and second positions, and a microprocessor cooperating with the oxygen sensor and the valve switching means having memory means provided with a selected reference product gas oxygen concentration at selected withdrawal rates from said reservoir, means for comparing the product gas oxygen concentration sensed by said oxygen sensor with said selected reference gas oxygen concentration, and means for adjusting the timing cycle for operating said switching means for pressurizing said sieve beds for a time required to produce product gas having at least said selected reference oxygen concentration.

24. The oxygen concentrator of claim 23 including a conduit extending between said sieve beds and a second valve cooperating therewith for directing product gas between said sieve beds and switching means for operating said valve to purge said sieve beds with product gas and wherein said microprocessor includes means for adjusting a timing cycle for operating said second valve.

25. The oxygen concentrator of claim 24 including control means cooperating with said oxygen sensor for selectively directing product gas and atmospheric air thereto.

26. The oxygen concentrator of claim 25 wherein said control means comprises a control valve electrically connected to said microprocessor for operating said control valve to direct product gas to said oxygen sensor at selected time intervals.

27. The oxygen concentrator of claim 26 wherein said control valve comprises a three-way valve having a first and second gas inlet and a gas outlet and means for selectively opening said first and second gas inlets.

28. In a process for selectively increasing the oxygen concentration of a gaseous mixture comprising switching a valve between a first position to direct atmospheric air under pressure from a compressor into a molecular sieve bed and selectively adsorbing nitrogen therefrom to produce an oxygen enriched product gas and a second position in which desorbed nitrogen is substantially removed from said sieve bed, directing said product gas to a reservoir, and withdrawing portions of said product gas from said reservoir, the improvement comprising:

(a) determining a preselected reference product gas oxygen concentration (b) intermittently sensing the oxygen concentration of product gas withdrawn from said reservoir, (c) comparing the sensed oxygen concentration of the product gas to the preselected reference oxygen concentration, and (d) if the sensed product gas oxygen concentration is less than said preselected reference oxygen concentration adjusting the timing cycle for switching said valve to increase the time for pressurizing said sieve bed until the sensed oxygen concentration of the product gas is at least equal to said preselected reference oxygen concentration.

29. In a process for selectively increasing the oxygen concentration of atmospheric air wherein a compressor alternately pressurizes a first and second sieve bed with atmospheric air, said sieve beds adsorbing nitrogen from atmospheric air to produce an oxygen enriched gaseous product and wherein said sieve beds are alternately charged by directing atmospheric air to a switching valve having a first valve position in which said compressor pressurizes said first sieve bed and nitrogen is substantially removed from said second sieve bed, and a second position in which said compressor pressurizes said second sieve bed and nitrogen is substantially removed from said first sieve bed, and directing said gaseous product from said sieve beds to a reservoir, the improvement comprising, (a) providing a timing cycle for switching said valve to said first and second positions, (b) determining a selected reference oxygen concentration for gaseous product at a specified delivery rate, (c) periodically sensing the oxygen concentration of said gaseous product and comparing the sensed concentration with said selected reference oxygen concentration, and (d) adjusting the timing cycle for switching said valve to increase the time for pressurizing said sieve bed when the sensed oxygen concentration is less than said selected reference concentration.

* * * * *